United States Patent
Seko et al.

(10) Patent No.: US 6,288,283 B1
(45) Date of Patent: Sep. 11, 2001

(54) PROCESS FOR PRODUCING RETINAL AND INTERMEDIATES FOR PRODUCING THE SAME

(75) Inventors: Shinzo Seko, Toyonaka; Naoto Konya, Takatsuki; Toshiya Takahashi, Ibaraki, all of (JP)

(73) Assignee: Sumitomo Chemical Company, Ltd., Osaka (JP)

( * ) Notice: Subject to any disclaimer, the term of this patent is extended or adjusted under 35 U.S.C. 154(b) by 0 days.

(21) Appl. No.: 09/584,354

(22) Filed: Jun. 1, 2000

(30) Foreign Application Priority Data

Jun. 3, 1999 (JP) ................................. H11-156396
Jun. 3, 1999 (JP) ................................. H11-156397

(51) Int. Cl.[7] ........................... C07C 47/11; C07C 45/34
(52) U.S. Cl. ........................... 568/447; 568/378; 568/470
(58) Field of Search ..................... 568/378, 447, 568/470

(56) References Cited

U.S. PATENT DOCUMENTS

| 2,766,290 | * | 10/1956 | Fletcher | 260/598 |
| 3,060,229 | * | 10/1962 | Eiter et al. | 260/488 |
| 4,148,829 | * | 4/1979 | Olson et al. | 260/601 |
| 5,087,762 | | 2/1992 | Mori et al. | |
| 5,118,866 | | 6/1992 | Knaus et al. | |

FOREIGN PATENT DOCUMENTS

| 63233943 | 9/1988 | (JP) . |
| 7103095 | 11/1995 | (JP) . |

OTHER PUBLICATIONS

Bienayme, H., Bull Soc. Chem Fr. (1995) 132, 696–708.
Hawkins, E. G. E. et al, The Strengths of Six Monocarboxylic Acids, etc., p. 411, 1944.
Mukaiyama T. et al, Chemistry Letters, pp. 1201–1202, 1975.
Karrer et al, Helv.Chim Acta, Fasciculus II, vol. 40, No. 34, pp. 265–266 (1957).

\* cited by examiner

Primary Examiner—Floyd D. Higel
Assistant Examiner—Ebenezer Sackey
(74) Attorney, Agent, or Firm—Birch, Stewart, Kolasch & Birch, LLP

(57) ABSTRACT

There are disclosed:

a hydroxyaldehyde derivative of formula (1):

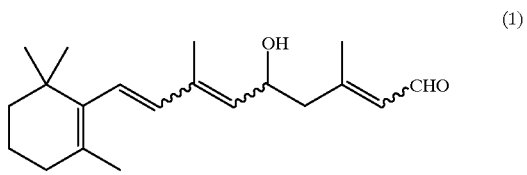

(1)

wherein the wavy line depicted by ⤳ indicates a single bond and the compound having a double bond to which said single bond is attached represents E or Z isomer or a mixture thereof, a methoxy alcohol derivative of formula (2):

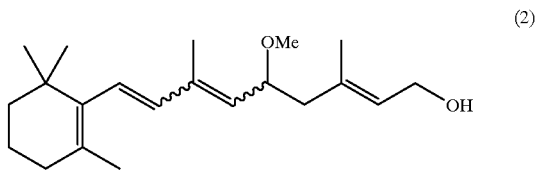

(2)

wherein the wavy line depicted by ⤳ indicates a single bond and the compound having a double bond to which said single bond is attached represents E or Z isomer or a mixture thereof, processes for producing the same, and a process for producing a retinal using the same.

18 Claims, No Drawings

PROCESS FOR PRODUCING RETINAL AND INTERMEDIATES FOR PRODUCING THE SAME

BACKGROUND OF THE INVENTION

1. Field of the Invention

The present invention relates to a process for producing retinal which is a basic starting material for producing carotenoids that is important in the fields of medicines, feed additives and food additives and it also relates to intermediates for producing retinal.

2. Description of Related Art

Retinal is an important basic starting material for producing carotenoids, e.g., β-carotene. As a method for the production of retinal, a method has been known, in which retinal is produced by oxidizing retinol (e.g., J. Chem. Soc. 411 (1944), JP63-233943A, Helv. Chim. Acta 40, 265 (1957) and JP7-103095B). However, this method has a problem in that it has required handling of retinol, which is sensitive to heat, light and oxygen. In addition to the above methods, the following methods are known, a method in which a carbon-increment reaction is conducted in the side chain of β-ionone which is a C13 compound (e.g., Bull. Soc. Chim. Fr. 132, 696 (1995)) and a method in which a carbon-increment reaction is conducted in a side chain of cyclocitral which is a C10 compound (Chem. Lett. 1201 (1975)). These methods, however, require, as a starting material, β-ionone or cyclocitral which is expensive on the market and produced by multistage processes. Hence, these methods are not always industrially satisfactory.

SUMMARY OF THE INVENTION

An object of the invention is to provide a process for producing retinal from relatively inexpensive starting material through an intermediate which is easy to handle, instead of labile retinol.

It is also an object of the invention to provide a novel intermediate compounds of formula (1) and (2) as well as processes for producing said intermediates from a diol derivative (3).

As shown in Scheme 1 said diol derivative (3) can be synthesized by treating a sulfone (8) with a base;

said sulfone (8) can be obtained by coupling a cyclic sulfone derivative (6) with an allyl halide derivative (7); and said cyclic sulfone derivative (6) and said allylhalide derivative (7) can be derivatized from linalool or geraniol which is a relatively inexpensive C10 compound.

Scheme 1

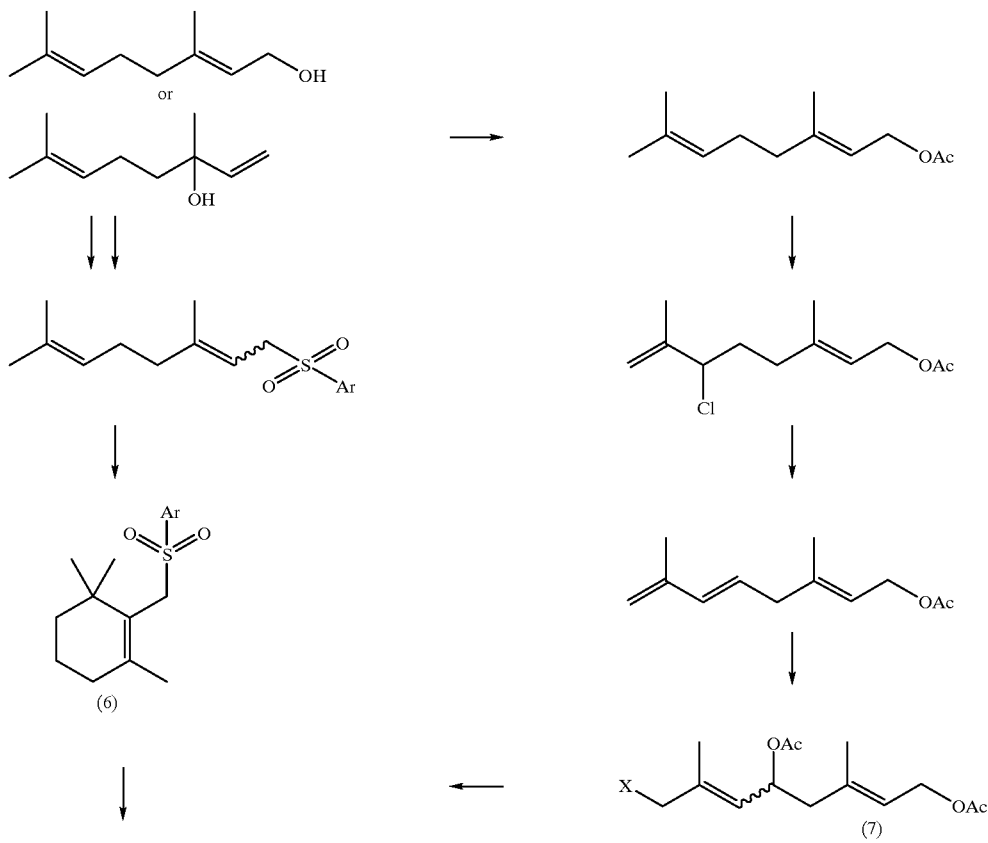

-continued

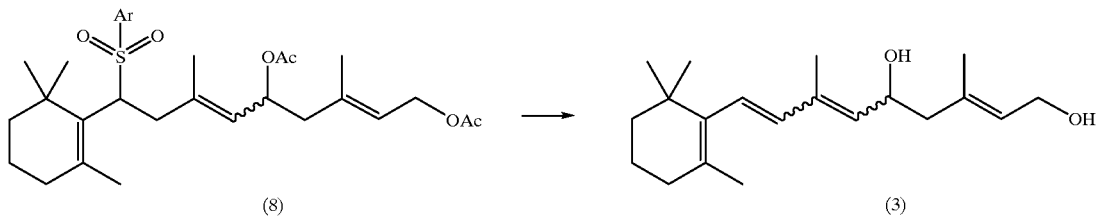

(8) → (3)

The method for producing the diol derivative (3) as shown in the scheme 1 is described in Chem. Lett. 479 (1975), JP11-130709A, JP11-130730A, JP11-222479A, JP11-236356A and JP11-236357A.

The present invention provides:

1. a hydroxyaldehyde derivative of formula (1):

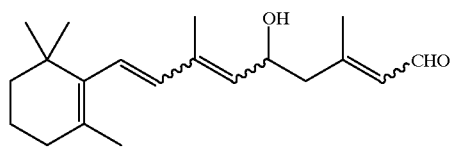

(1)

wherein the wavy line depicted by ~ indicates a single bond and the compound having a double bond to which said single bond is attached represents E or Z isomer or a mixture thereof, 2. a process for producing the hydroxyaldehyde derivative of formula (1) as defined above, which comprises oxidizing a diol derivative of formula (3):

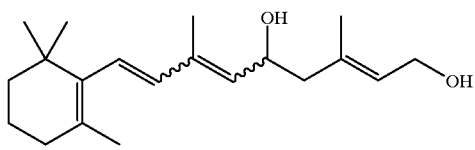

(3)

wherein the wavy line depicted by ~ indicates a single bond and the compound having a double bond to which said single bond is attached represents E or Z isomer or a mixture thereof, 3. a process for producing retinal of formula (4):

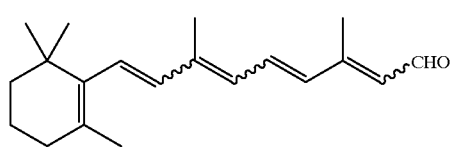

(4)

wherein the wavy line depicted by ~ indicates a single bond and the compound having a double bond to which said single bond is attached represents E or Z isomer or a mixture thereof, which comprises subjecting the hydroxyaldehyde derivative of formula (1) as defined above to a dehydrating reaction, 4. a methoxy alcohol derivative of formula (2):

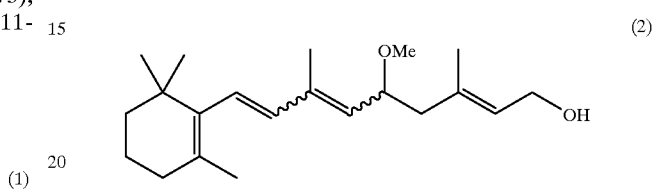

(2)

wherein the wavy line depicted by ~ indicates a single bond and the compound having a double bond to which said single bond is attached represents E or Z isomer or a mixture thereof.

5. a process for producing the methoxy alcohol derivative of formula (2) as defined above, which comprises selectively methylating a diol derivative of formula (3) as defined above, 6. a process for producing a methoxyaldehyde derivative of formula (5):

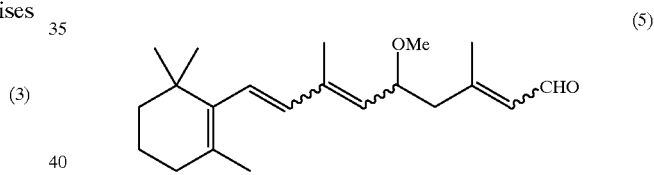

(5)

wherein the wavy line depicted by ~ indicates a single bond and the compound having a double bond to which said single bond is attached represents E or Z isomer or a mixture thereof, which comprises oxidizing a methoxy alcohol derivative of formula (2) as defined above, and 7. a process as defined in item 6 above, which further comprises the step of eliminating a methoxy group of the methoxyaldehyde derivative (5) to produce a retinal of formula (4) as defined above.

DESCRIPTION OF THE PREFERRED EMBODIMENTS

In the present invention, the wavy line depicted by ~ in formulae (1) to (8) indicates a single bond and the compound having a double bond to which said single bond is attached represents E or Z isomer or a mixture thereof. The hydroxyaldehyde derivative of formula (1) or the methoxy alcohol derivative of formula (2), for example, may represent a single geometrical isomer of all the possible isomers resulting from geometrical isomerism of each double bond to which a wavy line is attached or an optional mixture thereof.

The hydroxyaldehyde derivative (1) can be obtained by a process which comprises oxidizing the diol derivative (3) as defined above. In a similar manner, the methoxyaldehyde derivative of formula (5) also can be obtained by a process which comprises oxidizing the methoxy alcohol derivative of formula (2) and the following description refers to both the processes.

Oxidation of the diol derivative of formula (3) or the methoxy alcohol derivative of formula (2) is usually conducted with an oxidizing agent.

Examples of the oxidizing agent to be used include salts or oxides of metals such as chromium and manganese or a metal oxide of selenium. Specific examples thereof include pyridinium chlorochromate, pyridinium dichromate, manganese dioxide and selenium dioxide. The amount of the oxidizing agent is usually about 1 to 10 moles and preferably 1 to 3 moles per mol of the diol derivative (3) or the methoxy alcohol derivative of formula (2), respectively.

In the above reaction, an organic solvent is usually used. Examples of such a solvent include a hydrocarbon solvent such as n-hexane, cyclohexane, n-pentane, n-heptane, toluene or xylene, a halogenated solvent such as chloroform, dichloromethane, 1,2-dichloroethane, monochlorobenzene or o-dichlorobenzene, an aprotic solvent such as N,N-dimethylformamide, dimethyl sulfoxide, acetonitrile, N,N-dimethylacetamide or hexamethylphosphoric triamide, and an ether solvent such as 1,4-dioxane, tetrahydrofuran or anisole.

The oxidation reaction is usually conducted in a range from 0° C. to the boiling point of the solvent used.

After the reaction, the hydroxyaldehyde derivative (1) or the methoxyaldehyde derivative (5) can be obtained by a usual post-treatment such as filtration, extraction, evaporation or the like and may be further purified, for example, by silica gel chromatography, if necessary.

The hydroxyaldehyde derivative (1) can be derivatized to retinal (4) by a process which comprises dehydrating the hydroxyaldehyde derivative (1) in the presence of an acid catalyst.

Examples of the acid catalyst include triphenylphosphine hydrobromide, pyridine hydrochloride, pyridine hydrobromide, aniline hydrochloride, aniline hydrobromide, lutidine hydrochloride, lutidine hydrobromide, picoline hydrochloride, picoline hydrobromide, 2-pyridineethansulfonic acid, 4-pyridineethansulfonic acid, thionyl chloride-pyridine and paratoluenesulfonic acid-pyridine.

The amount of the acid catalyst to be used is preferably 0.05 to 2 moles per mol of the hydroxyaldehyde derivative (1).

In the above reaction, an organic solvent is usually used. Examples of the solvent include a hydrocarbon solvent such as n-hexane, cyclohexane, n-pentane, n-heptane, toluene or xylene, an ether solvent such as diethyl ether, tetrahydrofuran or anisole, a halogenated solvent such as chloroform, dichloromethane, 1,2-dichloroethane, monochlorobenzene or o-dichlorobenzene, and an aprotic solvent such as N,N-dimethylformamide, dimethyl sulfoxide, acetonitrile, N,N-dimethylacetamide or hexamethylphosphoric triamide.

The dehydration is usually conducted in a range from −10° C. to the boiling point of the solvent used and preferably in a range from about 0° C. to 100° C. After completion of the reaction, the desired product can be obtained by a usual post-treatment such as extraction, distillation and the like or may be further purified, for example by silica gel chromatography or the like, if necessary.

Next descriptions will be made to a process for producing the methoxy alcohol derivative (2), and a process for producing retinal of formula (4) from the methoxy alcohol derivative of formula (2) through the methoxyaldehyde derivative of formula (5).

The methoxy alcohol derivative (2) used in the present invention may be produced by a process which comprises reacting the diol derivative (3) with methanol in the presence of an acid catalyst, whereby selectively methylating a secondary alcoholic OH group of the diol derivative of formula (3).

Examples of the acid catalyst include a Lewis acid, Brönsted acid, heteropolyacid, acidic ion-exchange resin and acid chloride. More specifically, examples of Lewis acid include tin (II) chloride, tin (IV) chloride, zinc chloride, iron (III) chloride, boron trifluoride ether complex and rare earth metal triflate. Examples of Brönsted acid include hydrobromic acid, hydrochloric acid, sulfuric acid, paratoluenesulfonic acid, benzenesulfonic acid, methanesulfonic acid, benzoic acid, triphenylphosphine hydrobromide and pyridine hydrochloride. Examples of the acidic ion-exchange resin include a strong acid type having a sulfonic acid group at the terminal thereof The amount of the acid catalyst is preferably about 0.01 to 1 mol per mol of the diol derivative (3).

The reaction is usually conducted in a range of from −78° C. to the boiling point of the solvent to be used and preferably from −10° C. to 50° C.

After completion of the reaction, the methoxy alcohol derivative (2) can be obtained by a usual post-treatment such as extraction or the like, and may be further purified, for example, by silica gel chromatography, if necessary.

The methoxy alcohol derivative of formula (2) can be further oxidized to a corresponding methoxyaldehyde derivative of formula (5) by a process as described above.

The process for producing retinal of formula (4) from the methoxyaldehyde derivative (5) will be described below. The methoxyaldehyde derivative (5) is subjected to an elimination reaction to produce retinal (4). Said elimination reaction is usually conducted by a process which comprises contacting the methoxyaldehyde derivative of formula (5) with a base. The reaction can also be conducted by a method of Mukaiyama et al. in which DBU(1,8-diazabicyclo[5,4,0]undec-7-ene) is used as the base (Chem. Lett. 1201 (1975)). The base include a bicyclo tertiary amines such as DBU or DBN, which are preferably used. The amount of the amine is usually about 0.1 to 5 moles per mol of the methoxyaldehyde derivative of formula (5). Catalytic amount of the amine may be used, preferably in the co-presence of an alkali metal carbonate of which amount is 1 mol or more per mol of the methoxyaldehyde derivative of formula (5). Examples of the alkali metal carbonate include potassium carbonate and sodium carbonate.

In the above reaction, an organic solvent is usually used. Examples of the solvent include an ether solvent such as 1,4-dioxane, tetrahydrofuran and anisole, a hydrocarbon solvent such as n-hexane, cyclohexane, n-heptane, n-pentane, toluene or xylene, a halogenated solvent such as chloroform, dichloromethane, 1,2-dichloroethane, monochlorobenzene or o-dichlorobenzene, an aprotic solvent such as acetonitrile, N,N-dimethylformamide, dimethyl sulfoxide, N,N-dimethylacetamide or hexamethylphosphoric triamide.

The reaction is usually conducted in a range from −30° C. to the boiling point of the solvent used and preferably in a range from 20° C. to 100° C.

Thus, retinal of formula (4) can be obtained by the dehydration reaction of the hydroxyaldehyde derivative (1) using an acid catalyst or by the eliminating reaction of the methoxyaldehyde derivative (5) using a base, followed by a usual post-treatment.

According to the process of the present invention, retinal can be produced from the diol derivative (3) as starting material, which can be synthesized from the sulfones (8) obtained by coupling of the cyclic sulfone derivative (6) with the allyl halide derivative (7), both of which can be derived from a relatively inexpensive C10 compound such as linalool or geraniol without using retinol which is sensitive to heat, light and oxygen.

EXAMPLES

The present invention will be explained in more detail by way of examples, which are not to be construed to limit the invention thereto. Chemical formulae of the compounds (I), (II), (III), (IV) and (V) in the following Examples are shown below.

Example 1

1.22 g (4 mmol) of 1,5-dihydroxy-3,7-dimethyl-9-(2,6,6-trimethylcyclohexene-1-yl)-2,6,8-nonatriene (I) was dissolved in 30 ml of methylene chloride, to which was then added 3.48 g (40 mmol) of manganese dioxide and the mixture was stirred at an ambient temperature for 24 hours. After the resulting mixture was diluted with ether, it is dried over anhydrous magnesium sulfate and filtered, followed by evaporation of ether to obtain 5-hydroxy-3,7-dimethyl-9-(2,6,6-trimethylcyclohexene-1-yl)-nona-2,6,8-trienal (II) as a mixture of E and Z isomers in a yield of 90%.

Isomer (1)

1H-NMR δ(CDCl3) 1.00 (6H, s), 1.40–1.50 (2H, br), 1.50–1.75 (2H, br), 1.68 (3H, s), 1.88 (3H, s), 1.95–2.10 (2H, br), 2.24 (3H, s), 2.30–2.60 (2H, m), 4.70–4.90 (1H, m), 5.41 (1H, d, J=8Hz), 5.90–6.10 (2H, m), 6.16 (1H, d, J=16Hz), 10.00 (1H, d, J=8Hz).

Isomer (2)

1H-NMR δ(CDCl3) 1.00 (6H, s), 1.40–1.50 (2H, br), 1.50–1.75 (2H, br), 1.68 (3H, s), 1.90 (3H, s), 1.95–2.10 (2H, br), 2.22 (3H, s), 2.30–2.60 (2H, m), 4.70–4.90 (1H, m), 5.31 (1H, d, J=9Hz), 5.99 (1H, d, J=16Hz), 6.22 (1H, d, J=16Hz), 6.37 (1H, d, J=16Hz), 9.98 (1H, d, J=8Hz).

Example 2

605 mg (2 mmol) of 5-hydroxy-3,7-dimethyl-9-(2,6,6-trimethylcyclohexene-1-yl)-nona-2,6,8-trienal (II) was dissolved in 20 ml of toluene, to which were then added 57.8 mg (0.5 mmol) of pyridine hydrochloride and 39.5 mg (0.5 mmol) of pyridine and the mixture was stirred at 70° C. for 2 hours. After the mixture was cooled to an ambient temperature, water was added to the mixture. The resulting mixture was subjected to extraction with ether and the extract was dried over anhydrous magnesium sulfate, followed by evaporation of the solvent to obtain crude retinal. The resulting crude product was purified by neutral alumina column chromatography to obtain retinal (III) as a mixture of E and Z isomers in a yield of 46%.

Example 3

605 mg (2 mmol) of 5-hydroxy-3,7-dimethyl-9-(2,6,6-trimethylcyclohexene-1-yl)-nona-2,6,8-trienal (II) was dissolved in 6 ml of tetrahydrofuran, to which was then added 23.1 mg (0.2 mmol) of pyridine hydrochloride and the mixture was heated under reflux for 1 hour. After the mixture was cooled to an ambient temperature, water was added to the mixture. The resulting mixture was subjected to extraction with ether and the extract was dried over anhydrous magnesium sulfate, followed by evaporation of the solvent to obtain crude retinal. The resulting crude product was purified by neutral alumina column chromatography to obtain retinal (III) as a mixture of E and Z isomers in a yield of 48%.

Example 4

1.52 g (5 mmol) of 1,5-dihydroxy-3,7-dimethyl-9-(2,6,6-trimethylcyclohexene-1-yl)-2,6,8-nonatriene (I) was dissolved in 20 ml of methanol and the mixture was cooled to 0° C. To the mixture was then added 47.6 mg (0.25 mmol) of paratoluenesulfonic acid hydrate. After the mixture was stirred at 0° C. for 3 hours, a saturated aqueous sodium bicarbonate solution was added to the mixture and the resulting mixture was subjected to extraction with ether, followed by washing with a saturated brine. The resulting product was dried over anhydrous magnesium sulfate and the solvent was evaporated to obtain 1-hydroxy-5-methoxy-3,7-dimethyl-9-(2,6,6-trimethylcyclohexene- 1-yl) -2,6,8-nonatriene (IV) as a mixture of E and Z isomers in a yield of 85%.

1H-NMR δ(CDCl3) 1.01 (6H, s), 1.45–1.48 (2H, br), 1.60–1.72 (2H, br), 1.69 (3H, s), 1.72 (3H, s), 1.84 (3H, s), 1.98–2.05 (2H, br), 2.05–2.44 (2H, m), 3.25 (3H, m), 4.12–4.21 (3H, m), 5.13–5.26 (1H, m), 5.44–5.49 (1H, m), 6.05–6.67 (2H, m).

Example 5

1.34 g (4.2 mmol) of 1-hydroxy-5-methoxy-3,7-dimethyl-9-(2,6,6 -trimethylcyclohexene-1-yl)-2,6,8-nonatriene (IV) was dissolved in 40 ml of methylene chloride, to which was then added 3.66 g (42 mmol) of manganese dioxide and the mixture was stirred at an ambient temperature for 24 hours. After the resulting mixture was diluted with an ether, it was dried over anhydrous magnesium sulfate and filtered, followed by evaporation of the solvent to obtain 5-methoxy-3,7-dimethyl-9-(2,6,6-trimethylcyclohexene-1-yl)-nona-2,6,8-trienal (V) as a mixture of E and Z isomers in a yield of 91%.

1H-NMR δ(CDCl3) 1.01 (6H, s), 1.41–1.50 (2H, br), 1.50–1.75 (2H, br), 1.69 (3H, s), 1.86 (3Hx 72/100, s), 1.93 (3Hx 28/100, s), 1.95–2.10 (2H, br), 2.18 (3Hx 28/100, s), 2.21 (3Hx 72/100, s), 2.31–2.56 (2H, m), 3.24 (3Hx 28/100, s), 3.26 (3Hx 72/100, s), 4.23–4.35 (1H, m), 5.12–5.30 (1H, m), 5.92–6.40 (3H, m), 9.99 (1Hx 28/100, d, J=7Hz), 10.02 (1Hx 72/100, d, J=7Hz).

Example 6

633 mg (2 mmol) of 5-methoxy-3,7-dimethyl-9-(2,6,6-trimethylcyclohexene-1-yl)-nona-2,6,8-trienal (V) was dissolved in 6 ml of tetrahydrofuran, to which was then added 152 mg (1 mmol) of 1,8-diazabicyclo[5,4,0]undecene-7-ene (DBU) and the mixture was heated under reflux for 6 hours. After the reaction, the solvent was evaporated to give a crude product. The resulting crude product was purified by silica gel chromatography to obtain retinal (III) as a mixture of E and Z isomers in a yield of 55%.

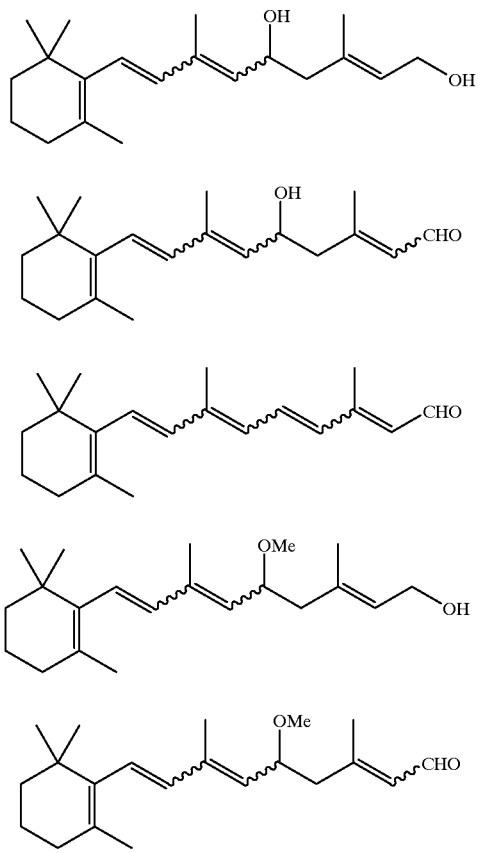

What is claimed is:

1. A hydroxyaldehyde derivative of formula (1):

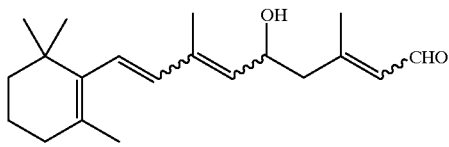

wherein the wavy line depicted by ⁓ indicates a single bond and the compound having a double bond to which said single bond is attached represents E or Z isomer or a mixture thereof.

2. A methoxy alcohol derivative of formula (2):

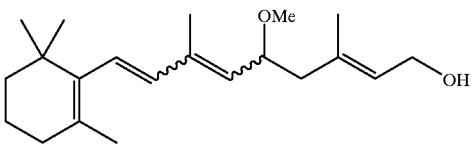

wherein the wavy line depicted by ⁓ indicates a single bond and the compound having a double bond to which said single bond is attached represents E or Z isomer or a mixture thereof.

3. A process for producing a methoxy alcohol derivative of formula (2) as defined in claim 2, which comprises selectively methylating a diol derivative of formula (3):

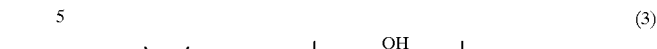

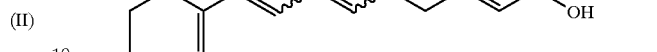

wherein the wavy line depicted by ⁓ indicates a single bond and the compound having a double bond to which said single bond is attached represents E or Z isomer or a mixture thereof.

4. A process for producing a methoxyaldehyde derivative of formula (5):

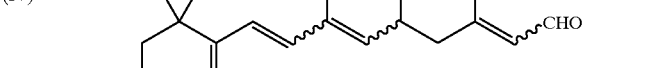

wherein the wavy line depicted by ⁓ indicates a single bond and the compound having a double bond to which said single bond is attached represents E or Z isomer or a mixture thereof, which comprises oxidizing a methoxy alcohol derivative of formula (2) as defined in claim 2.

5. A process according to claim 3, which further comprises the step of oxidizing the methoxy alcohol derivative (2) to produce a methoxyaldehyde derivative of formula (5):

wherein the wavy line depicted by ⁓ indicates a single bond and the compound having a double bond to which said single bond is attached represents E or Z isomer or a mixture thereof.

6. A process according to claim 5, which further comprises eliminating a methoxy group of the methoxyaldehyde derivative (5) to produce a retinal of formula (4):

wherein the wavy line depicted by ⁓ indicates a single bond and the compound having a double bond to which said single bond is attached represents E or Z isomer or a mixture thereof.

7. A process according to claim 4 which further comprises the step of eliminating a methoxy group of the methoxyaldehyde derivative (5) to produce a retinal of formula (4):

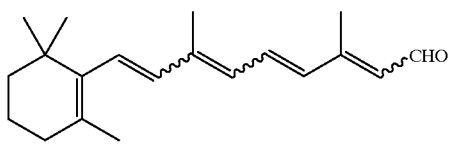
(4)

wherein the wavy line depicted by ～ indicates a single bond and the compound having a double bond to which said single bond is attached represents E or Z isomer or a mixture thereof.

8. A process for producing a hydroxyaldehyde compound of formula (1) as defined in claim 1, which comprises oxidizing a diol compound of formula (3):

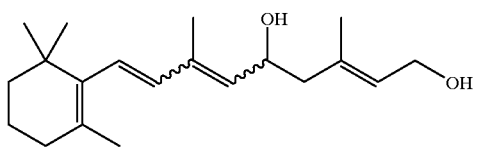
(3)

wherein the wavy line depicted by ～ indicates a single bond and the compound having a double bond to which said single bond is attached represents E or Z isomer or a mixture thereof, with a metal oxide.

9. A process for producing a hydroxyaldehyde compound of formula (1) as defined in claim 1, which comprises contacting a diol compound of formula (3):

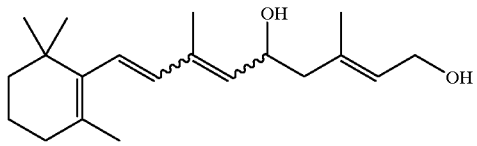
(3)

wherein the wavy line depicted by ～ indicates a single bond and the compound having a double bond to which said single bond is attached represents E or Z isomer or a mixture thereof, with an oxidizing agent.

10. A process according to claim 9, wherein said oxidizing agent is an oxidizing agent selected from an oxide of chromium, manganese, or selenium, or a salt of chromium or manganese.

11. A process according to claim 9, wherein said oxidizing agent is pyridinium chlorochromate, pyridinium dichromate, or selenium dioxide.

12. A process for producing retinal of formula (4):

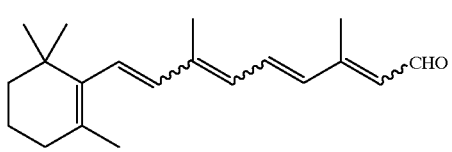
(4)

wherein the wavy line depicted by ～ indicates a single bond and the compound having a double bond to which said single bond is attached represents E or Z isomer or a mixture thereof, which comprises contacting a hydroxyaldehyde compound of formula (1) as defined in claim 1 to a dehydrating reaction with an acid catalyst.

13. A process for producing retinal of formula (4):

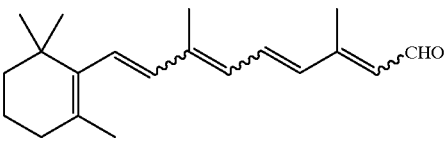
(4)

wherein the wavy line depicted by ～ indicates a single bond and the compound having a double bond to which said single bond is attached represents E or Z isomer or a mixture thereof, which comprises contacting a hydroxyaldehyde compound of formula (1) as defined in claim 1 with an acid catalyst.

14. A process according to claim 13, wherein said acid catalyst is triphenylphosphine hydrobromide, pyridine hydrochloride, pyridine hydrobromide, aniline hydrochloride, aniline hydrobromide, lutidine hydrochloride, lutidine hydrobromide, picoline hydrochloride, picoline hydrobromide, 2-pyridineethansulfonic acid, 4-pyridineethansulfonic acid, thionyl chloride-pyridine, or p-toluenesulfonic acid-pyridine.

15. A process according to claim 8 or 9, which further comprises the step of subjecting the hydroxyaldehyde compound (1):

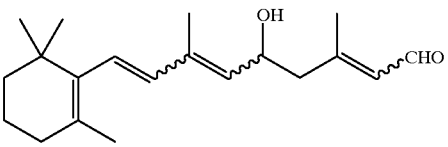
(1)

wherein the wavy line depicted by ～ indicates a single bond and the compound having a double bond to which said single bond is attached represents E or Z isomer or a mixture thereof, to a dehydrating reaction with an acid catalyst to produce a retinal of formula (4):

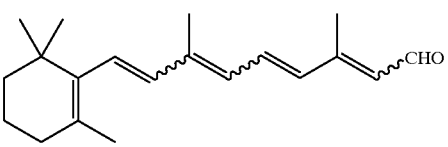
(4)

wherein the wavy line depicted by ～ indicates a single bond and the compound having a double bond to which said single bond is attached represents E or Z isomer or a mixture thereof.

16. A process according to claim 8 or 9, which further comprises the step of contacting the hydroxyaldehyde compound (1):

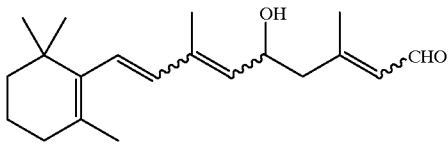 (1)

wherein the wavy line depicted by ∿ indicates a single bond and the compound having a double bond to which said single bond is attached represents E or Z isomer or a mixture thereof, with an acid catalyst to produce a retinal of formula (4):

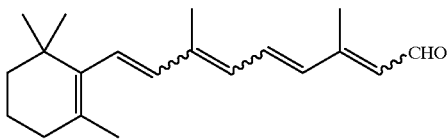 (4)

wherein the wavy line depicted by ∿ indicates a single bond and the compound having a double bond to which said single bond is attached represents E or Z isomer or a mixture thereof.

17. A process according to claim 15, wherein said acid catalyst is triphenylphosphine hydrobromide, pyridine hydrochloride, pyridine hydrobromide, aniline hydrochloride, aniline hydrobromide, lutidine hydrochloride, lutidine hydrobromide, picoline hydrochloride, picoline hydrobromide, 2-pyridineethansulfonic acid, 4-pyridineethansulfonic acid, thionyl chloride-pyridine, or p-toluenesulfonic acid-pyridine.

18. A process according to claim 16, wherein said acid catalyst is triphenylphosphine hydrobromide, pyridine hydrochloride, pyridine hydrobromide, aniline hydrochloride, aniline hydrobromide, lutidine hydrochloride, lutidine hydrobromide, picoline hydrochloride, picoline hydrobromide, 2-pyridineethansulfonic acid, 4-pyridineethansulfonic acid, thionyl chloride-pyridine, or p-toluenesulfonic acid-pyridine.

* * * * *